(12) United States Patent
Carite et al.

(10) Patent No.: US 11,648,204 B2
(45) Date of Patent: May 16, 2023

(54) PROCESS FOR LYOPHILISING A PRODUCT

(71) Applicant: 4D Pharma León S.L.U., Leon (ES)

(72) Inventors: Christophe Carite, Leeds (GB);
Sophie Declomesnil, Leeds (GB)

(73) Assignee: 4D Pharma León S.L.U., Leon (ES)

( * ) Notice: Subject to any disclaimer, the term of this patent is extended or adjusted under 35 U.S.C. 154(b) by 77 days.

(21) Appl. No.: 17/410,395

(22) Filed: Aug. 24, 2021

(65) Prior Publication Data

US 2022/0031621 A1 Feb. 3, 2022

Related U.S. Application Data

(63) Continuation of application No. 16/742,367, filed on Jan. 14, 2020, now Pat. No. 11,135,168, which is a
(Continued)

(30) Foreign Application Priority Data

Jul. 14, 2017 (GB) ...................................... 1711359

(51) Int. Cl.
*A61K 9/19* (2006.01)
*A61K 9/48* (2006.01)
(Continued)

(52) U.S. Cl.
CPC .................. *A61K 9/19* (2013.01); *A61K 9/48* (2013.01); *A61K 35/74* (2013.01); *F26B 5/06* (2013.01);
(Continued)

(58) Field of Classification Search
CPC .. F26B 5/06; F26B 5/10; F26B 25/002; F26B 25/16; A61K 9/19; A61K 9/48; A61K 35/74
(Continued)

(56) References Cited

U.S. PATENT DOCUMENTS

| 1,053,936 A | * | 2/1913 | Van Valkenburg | ....... G10F 1/02 84/62 |
| 4,022,206 A | | 5/1977 | Hilleman et al. | |

(Continued)

FOREIGN PATENT DOCUMENTS

| CA | 1232549 A | 2/1988 |
| CN | 104081142 A | 10/2014 |

(Continued)

OTHER PUBLICATIONS

Mar. 9, 2021 Non-Final Office Action U.S. Appl. No. 16/742,367.

*Primary Examiner* — Stephen M Gravini

(74) *Attorney, Agent, or Firm* — Wilson Sonsini Goodrich & Rosati

(57) ABSTRACT

The present invention relates to a process for lyophilising a product (3), comprising the steps of providing a bulk product (3) loading system in the form of a bag (1), the bag (1) having an interior and an exterior defined by a flexible wall, the bag (1) further comprising a filling port (5) providing access to the interior of the bag (1), filling a product (3) having a first moisture content into the interior of the bag (1) via the filling port (5), and exposing the product (3) in the interior of the bag (1) to a lyophilisation cycle such that the moisture content of the product (3) is reduced from the first moisture content to a second, lower, moisture content.

20 Claims, 6 Drawing Sheets

Related U.S. Application Data continuation of application No. PCT/IB2018/055246, filed on Jul. 16, 2018.

(51) Int. Cl.

| | | |
|---|---|---|
| *A61K 35/74* | (2015.01) | |
| *F26B 5/06* | (2006.01) | |
| *F26B 5/10* | (2006.01) | |
| *F26B 25/00* | (2006.01) | |
| *F26B 25/16* | (2006.01) | |

(52) U.S. Cl.
CPC .............. *F26B 5/10* (2013.01); *F26B 25/002* (2013.01); *F26B 25/16* (2013.01)

(58) Field of Classification Search
USPC .......................................................... 34/284
See application file for complete search history.

(56) References Cited

U.S. PATENT DOCUMENTS

| | | |
|---|---|---|
| 4,035,924 A | 7/1977 | Faure |
| 4,132,848 A | 1/1979 | Cise et al. |
| 4,973,327 A | 11/1990 | Goodrich, Jr. et al. |
| 5,257,983 A | 11/1993 | Garyantes et al. |
| 5,727,333 A | 3/1998 | Folan |
| 5,884,414 A | 3/1999 | Anger |
| 5,947,274 A | 9/1999 | Taskis et al. |
| 6,381,967 B1 | 5/2002 | Craig |
| 7,200,954 B2 | 4/2007 | Watanabe et al. |
| 8,171,652 B2 | 5/2012 | Py |
| 8,449,520 B2 | 5/2013 | Pepper et al. |
| 8,518,452 B2 | 8/2013 | Bjornstrup et al. |
| 8,549,768 B2 | 10/2013 | Chakravarty et al. |
| 8,919,007 B2 | 12/2014 | Friess et al. |
| 9,222,728 B2 | 12/2015 | Py |
| 9,651,305 B2 | 5/2017 | Gasteyer et al. |
| 10,139,162 B2 | 11/2018 | Plavnik et al. |
| 10,539,367 B2 | 1/2020 | Corbin, III et al. |
| 10,809,002 B2 | 10/2020 | Schuetz |
| 11,135,168 B2 * | 10/2021 | Carite ................. F26B 25/16 |
| 11,523,969 B2 * | 12/2022 | Vedrine ................ A61J 1/1468 |
| 2003/0121171 A1 | 7/2003 | Chou |
| 2008/0229609 A1 | 9/2008 | Bronshtein |
| 2009/0113753 A1 | 5/2009 | Pepper et al. |
| 2014/0047851 A1 | 2/2014 | Zhou et al. |
| 2015/0354894 A1 | 12/2015 | Corbin, III et al. |
| 2020/0103323 A1 | 4/2020 | Plochinger |
| 2020/0179289 A1 | 6/2020 | Carite et al. |
| 2022/0031621 A1* | 2/2022 | Carite ................. A61K 9/19 |

FOREIGN PATENT DOCUMENTS

| | | | | |
|---|---|---|---|---|
| CN | 106461327 A | | 2/2017 | |
| EP | 0426475 A1 | | 5/1991 | |
| EP | 0914813 A2 | | 5/1999 | |
| EP | 1053936 A1 | * | 11/2000 | ............. B64D 27/26 |
| EP | 1788076 A1 | | 5/2007 | |
| EP | 1958618 A1 | | 8/2008 | |
| EP | 2431024 A1 | | 3/2012 | |
| EP | 3254039 B1 | | 4/2020 | |
| GB | 2564481 A | * | 1/2019 | ............. A61K 35/74 |
| GB | 2564481 B | | 10/2019 | |
| JP | H05306216 A | | 11/1993 | |
| JP | H10305083 A | | 11/1998 | |
| JP | 2001106242 A | | 4/2001 | |
| JP | 2007135591 A | | 6/2007 | |
| KR | 2011028926 A | * | 3/2011 | |
| WO | WO-9631748 A1 | | 10/1996 | |
| WO | WO-2005053721 A1 | | 6/2005 | |
| WO | WO-2008099016 A3 | | 11/2008 | |
| WO | WO-2010019217 A1 | | 2/2010 | |
| WO | WO-2016125095 A1 | | 8/2016 | |
| WO | WO-2019012512 A1 | | 1/2019 | |

\* cited by examiner

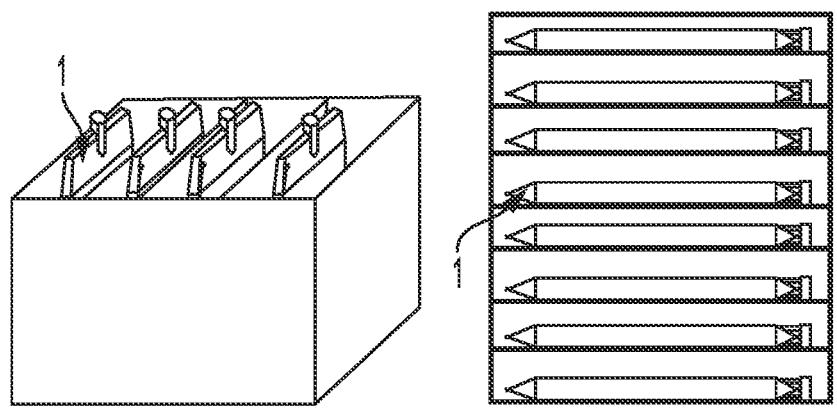
FIG. 3
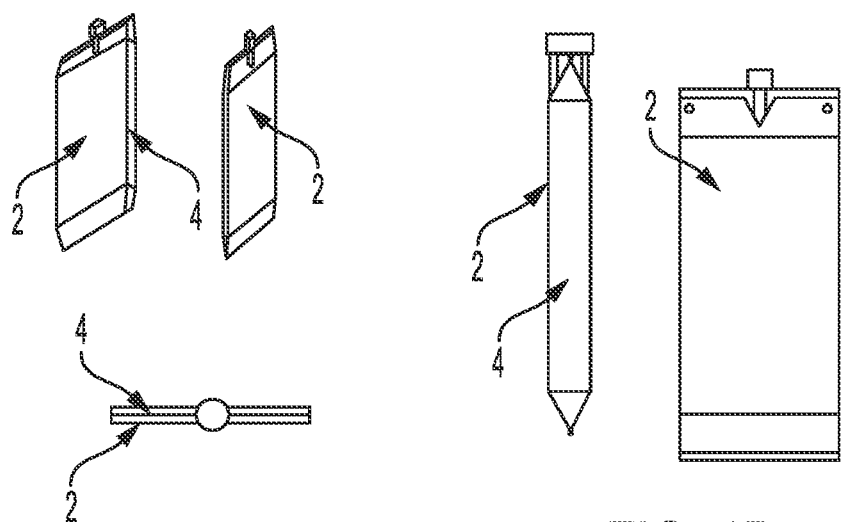
FIG. 4A
FIG. 4B

PROCESS FOR LYOPHILISING A PRODUCT

CROSS-REFERENCE

This application is a continuation of U.S. application Ser. No. 16/742,367, filed Jan. 14, 2020, now U.S. Pat. No. 11,135,168, issued Oct. 5, 2021, which is a continuation of International Application No. PCT/IB2018/055246, filed Jul. 16, 2018, which claims the benefit of Great Britain Application No. 1711359.8, filed Jul. 14, 2017, all of which are hereby incorporated by reference in their entirety.

FIELD OF THE INVENTION

The present invention relates to processes and apparatus for reducing contamination, such that products can be lyophilised in an efficient and economic manner.

BACKGROUND TO THE INVENTION

Lyophilisation is a widely used process for formulating pharmaceutical, biotechnological and other types of product. It is an effective way to prepare solid products, even if those products are pharmaceutical products which are destined to be administered in liquid form to patients. Lyophilisation is also a convenient way to produce preparations containing live organisms, or chemically sensitive products obtained from organisms.

While there are many commercially operated lyophilisation processes, these typically involve three phases, namely i) freezing, ii) primary drying or sublimation and iii) secondary drying or desorption.

During the freezing phase and optionally also during the sublimation phase, the product is frozen, typically between $-20°$ C. and $-80°$ C. Once the product has attained the target reduced temperature, the pressure to which it is exposed is reduced, and a moderate amount of heat is applied, which causes the frozen water present in the product to sublime. This first step of the lyophilisation process generally results in the majority of the water present in the product being removed.

In the third phase, desorption, the temperature is increased to remove any non-frozen water molecules present in the product.

Generally speaking, effectively operated lyophilisation processes can be used to produce products having a very low water content, e.g. less than 5%.

On a pilot scale or on an industrial scale, lyophilisation is commonly carried out in freeze dryers. Freeze dryers conventionally include the following components: a) a vacuum pump to reduce the pressure in the dryer; and b) a condenser to remove moisture from the freeze dryer by condensation. Differences exist between freeze dryers in terms of how the product to be lyophilised is arranged.

In freeze dryers conventionally used in the preparation of pharmaceutical or biotechnological products, the product to be lyophilised may be loaded into the freeze dryer in bulk. In such arrangements, the bulk product is placed in trays and the trays are then loaded into the freeze dryer for lyophilisation.

The trays are generally shaped to maximise the surface area of the product which is exposed to the interior of the freeze dryer to facilitate sublimation and desorption of water from the product.

While trays of this type have been used effectively for many years, their use is not appropriate for the preparation of all types of product.

More specifically, in some circumstances, the consequences of cross-contamination between batches of products used with the same freeze dryer may be of particular concern, for example where the freeze dryer has been previously used with high potency products, such as drugs (where trace amounts of such a product could taint a subsequently processed batch of product to produce an observable effect on end users or patients), or bacterial products (where single organisms could contaminate batches of subsequently produced products).

A further disadvantage with conventional steel or plastic freeze dryer trays is that between freeze drying batches of product, the trays must be removed from the freeze dryer, cleaned thoroughly and, in some cases, sterilised. Such cleaning/sterilisation steps are time-consuming. Further, there is a risk that imperfect cleaning of the trays between batches could be a further cause of cross-contamination.

A variation of conventional trays has been commercialised. Lyoguard® trays, marketed by Gore®, are specifically developed freeze drying trays. They comprise flexible plastic bases with rigid upstanding walls to provide structure to the tray. The tray is closed by an upper surface constructed from a water permeable membrane, enabling the egress of moisture from product within the interior of the tray during lyophilisation.

The Lyoguard® tray is also fitted with a filling port on its upper surface, through which product can be placed into the tray. Once the tray has been filled, the filling port is closed with a threaded closure and the filled tray can be loaded into the freeze dryer to lyophilise the product.

While the Lyoguard® tray has enjoyed commercial success, there are a number of shortcomings associated with its use. Firstly, the water permeable membrane which closes the tray is relatively fragile and prone to damage. In commercial scale lyophilisation operations, many such trays will be filled and stacked in advance of being loaded into the freeze dryer. Despite care being taken by the operatives working with the freeze dryer, there is the risk that, through improper stacking, or as a result of other items being placed on top of filled Lyoguard® trays, the water permeable membrane could be pierced or torn.

Additionally, while the moisture permeable membrane permits the egress of moisture from the interior of the Lyoguard® tray, the membrane is not of a 'one-way' construction and, thus, re-entry of moisture back into the interior of the tray from the exterior can occur.

Further, especially when the product to be lyophilised is particulate, the membrane can become clogged with the product, minimising its moisture permeability.

Owing to its construction, it has been found that distributing the product to be lyophilised across the interior of the tray evenly can be challenging. This can lead to non-uniform freezing resulting in pockets of the finished product comprising an unacceptably high moisture content.

Additionally, the capacity of the standard Lyoguard® tray is limited and, in practice, it is challenging to effectively lyophilise quantities of product of greater than 1 kg.

Depending on the product to be lyophilised, a further issue of concern to some users is that, owing to the gas permeability of the upper surface, the interior of the tray cannot be purged or maintained under vacuum, which can be problematic for example if the material to be lyophilised is anaerobic.

A further disadvantage associated with the Lyoguard® tray is its cost. Owing to its relatively complex structure, presumably, the cost per tray is high. This, coupled with the susceptibility of the Lyoguard® and its relatively modest loading capacity means that there is a demand for lyophilisation trays or bulk loading systems which provide the product to be lyophilised with protection from contamination, which are resistant to damage, which permit substantial quantities of product to be lyophilised and/or which permit the economic lyophilisation of products.

SUMMARY OF THE INVENTION

Thus, according to a first aspect of the present invention, there is provided a process for lyophilising a product comprising providing a bulk product loading system in the form of a bag, the bag having an interior and an exterior defined by a flexible wall, the bag further comprising a filling port providing access to the interior of the bag; filling a product having a first moisture content into the interior of the bag via the filling port; and exposing the product in the interior of the bag to a lyophilisation cycle such that the moisture content of the product is reduced from the first moisture content to a second, lower, moisture content.

As mentioned above, the bulk loading system for use in the present invention is in the form of a bag. The bag comprises a flexible wall.

The wall of the bag may be of any thickness provided that the bag retains an acceptable resistance to damage and is capable of securely containing the product to be lyophilised, while retaining acceptable flexibility. In particular, the flexible wall of the bag may have a thickness ranging from about 0.1 µm to about 500 µm, preferably between about 10 µm to about 200 µm, or preferably between about 50 µm to about 150 µm.

Additionally or alternatively, in the process of the present invention, the wall of the bag may be a single layer or have a multi-layer construction, for example, comprising 2, 3, 4, 5, 6, 7, 8 or more layers. Where reference is made herein to an "inner layer" of the bag, this relates to the innermost layer which defines the interior of the bag. Where the reference is made to an "outer layer" of the bag, this relates to the outermost layer which defines the exterior of the bag. Where the wall of the bag has a single layer construction, that layer will be both the inner and outer layer of the bag. In multi-layer constructions, the material from which each layer is prepared may be the same as one another, or may be different from the material from which at least one of the other layers is prepared.

The bag may be formed from a range of materials with which one skilled in the art will be familiar. The material or materials from which the bag is formed must be sufficiently robust such that it is, or they are, not seriously damaged by the conditions to which it or they will be exposed during lyophilisation, filling and/or shipment. The material(s) from which the bag is formed may be selected in order to provide the bag with certain properties. For example, the material from which the inner layer of the wall is formed may be heat sealable at temperatures of less than about 150° C., less than about 130° C., less than about 110° C. or less than about 90° C. Additionally or alternatively, the material from which the inner layer is formed may be compliant with the US and/or European Pharmacopeia.

During lyophilisation, the bag may be exposed to low temperatures, for example temperatures of between −50° C. and −80° C. Consequently, the material from which the bag is formed may be resistant to damage at such low temperatures.

Examples of materials that may be used to from the inner layer of the bag include polymeric materials such as polyethylene (e.g. HDPE, MDPE, LDPE or VLDPE), polyethylene terephthalate (PET), and PET-aluminium-OPA.

The outer layer of the bag may be formed from a material which does not soften at conventional heat sealing temperatures, for example which has a softening point greater than about 90° C., about 110° C., about 130° C., or about 150° C.

When a multi-layered bag construction is employed, one or more (e.g. 1, 2, 3, 4, 5 or more) intermediate layers may be present, i.e. layers disposed between the inner and outer layers. The intermediate layer(s) may be selected to impart properties to the bag. For example, the bag may comprise a barrier layer that may be an intermediate (or inner or outer) layer of the bag. Such a barrier layer may limit transmission of moisture, oxygen and/or light through the wall of the bag. Examples of materials from which the barrier layer may be formed include metallic or metallised materials, for example, aluminium and polypropylene.

Overall, the wall of the bag may exhibit certain desirable properties. In embodiments of the invention the bag may be sterilisable, e.g. it may be capable of sterilisation via ionising (e.g. gamma and/or beta) irradiation, steam treatment, heat treatment e.g. by autoclave, and/or chemical treatment, e.g. with isopropyl alcohol. Thus, the process may include the additional step of sterilising the bag (or at least its exterior) prior to loading into a lyophiliser.

Additionally or alternatively, the wall of the bag may have certain barrier properties. For example, the bag may be opaque.

Additionally or alternatively, the wall of the bag may have high moisture transmissivity in order to facilitate the egress of moisture from the bag during lyophilisation. In such embodiments, the Water Vapour Transmissivity Rate ("WVTR", in units of $g \cdot m^{-2} \cdot d^{-3}$) may be at least about 500, at least about 750, at least about 1000, at least about 1500, or at least about 2000. Alternatively, a less moisture permeable bag construction may be preferred. In such embodiments, the WVTR may be less than about 100, less than about 50, less than about 20, less than about 10, less than about 5, less than about 2, less than about 1, less than about 0.5, less than about 0.2 or less than about 0.1 $g \cdot m^{-2} \cdot d^{-3}$. Thus, when the bag closure means are closed, the bag may be essentially impervious to moisture.

The product to be filled into the bag may comprise any material requiring lyophilisation. For example, the product may comprise a pharmaceutical or biotechnological active principle and optionally one or more excipients, such as lyoprotectants, fillers or the like. The product to be lyophilised may be sterilised prior to or following filling of the bag.

The product may comprise live cells, such as bacterial or fungal cells. These may be a single strain of cells or cells belonging to a single species. Alternatively, a mixture of cells may be present.

As mentioned above, the bag used in the present invention is provided with a filling port. The primary purpose of the filling port is to provide access to the interior of the bag to enable the bag to be filled with product to be lyophilised.

The filling port may take any form needed to fulfil this requirement. For example, the filling port may take the form of a simple opening in the wall of the bag. The opening may be of any suitable shape, size or dimension. Preferably, the bag is sized to facilitate loading into a lyophiliser.

The filling port may be provided with a collar. This may be a separate component which is joined to the bag (e.g. via adhesion or welding). Alternatively, the collar may be provided by a thickened portion of the bag wall surrounding an opening in the bag wall. In any case, the collar may comprise an upstanding wall, defining the filling port. The collar may have a substantially cylindrical construction e.g. with a diameter of about 0.5 cm to about 20 cm, about 1 cm to about 10 cm, or about 2 cm to about 5 cm.

The filling port may be provided with coupling means, for example, to enable the bag to be connected to filling apparatus exterior of the bag which can be used to fill the bag with the product to be lyophilised. Additionally or alternatively, the coupling means may permit the bag to connect to drying apparatus and/or means to supply inert gas into the interior of the bag.

The filling port may also be provided with closure means, to permit the bag to be closed prior to or following lyophilisation. Such closure means may comprise a closure that can be connected to the bag or the filling port to close the filling port. The closure may be a cap, flap, patch, lid or the like that is connectable to the bag or the filling port, e.g. via threading, friction fit, snap fit, adhesion or the like.

When the bag includes closure means, the bag may be closed prior to lyophilisation.

The interior of the bag may be sterilised prior to use, e.g. via ionising (e.g. gamma and/or beta) irradiation, steam treatment and/or heat treatment. The bag, if provided with closure means, may then be closed, prior to being opened at the time at which the bag is to be filled.

Additionally or alternatively, the interior of the bag may be purged prior to use, for example by nitrogen flushing or the administration of a vacuum. This may be particularly advantageous where the product to be lyophilised is anaerobic.

Additionally or alternatively, the interior of the bag provided in the first step of the process may be sterile and/or the bag, if provided with closure means, may be closed. If the bag is provided with the filling port closed, the process of the invention may include the step of opening the filling port prior to filling the interior of the bag with the product to be lyophilised.

During the lyophilisation cycle, the bag will typically be placed on a refrigerated shelf which then cools the product in the bag. An even transfer of cooling to the product in the bag is best achieved when the product has a uniform thickness. If the thickness is uneven regions of the material may be cooled (and thus dried) less. To maximise drying of the product within the bag during lyophilisation, the bag may be shaped to evenly distribute the product within the bag such that the thickness or depth of the product within the bag is relatively uniform. This may be achieved through the use of a bag comprising two generally planar panels spaced apart by a side wall, the side wall preferably being of constant height such that, when the bag is filled, the panels are substantially coplanar. The side wall may be provided by lateral gussets in the bag. Configuring the bag in this way is advantageous as it makes it possible to achieve uniform thickness or depth of the product to be lyophilised regardless of the orientation of the bag during filling and loading.

In some embodiments, the two generally planar panels are semi-rigid or rigid.

The bag may have a flattened profile prior to filling.

The side wall may have a height which is no more than about 50%, no more than about 40%, no more than about 30%, no more than about 20%, no more than about 15% or no more than about 10% of the length of the next shortest dimension of the bag (e.g. its length or width, whichever is shorter).

Additionally or alternatively, the side wall of the bag, when filled, may be greater than about 0.5 cm, greater than about 1 cm, greater than about 1.5 cm, greater than about 2 cm, greater than about 3 cm, greater than about 5 cm, greater than about 7 cm, greater than about 10 cm or greater than about 15 cm.

The bag may be formed in many different shape. In particular, when viewed from above, the bag may have a square, rectangular, circular, or other shape.

It has been found that the process of the present invention can advantageously be carried out using batches of product in excess of 1 kg per bag. Thus, the amount of product placed into the bag may be about 1 kg or more, about 1.5 kg or more, about 2 kg or more, about 2.5 kg or more, about 3 kg or more, about 4 kg or more, or about 5 kg or more. The only constraint on the amount of product to be lyophilised according to the process of the present invention is the internal capacity of the freeze dryer in which the lyophilisation is carried out. Thus, the bag may be filled with about 50 kg or less, about 20 kg or less, or about 10 kg or less of product.

The bag may be produced by any suitable means known to those skilled in the art. For example, the bag may be formed by blowing a polymeric material. Alternatively, the bag may be formed by sealing two coplanarly arranged sheets or panels of material according to a predetermined pattern. In that case, sealing may be achieved by heat sealing, cold sealing, adhesive sealing, welding or the like.

The interior of the bag may be exposed to a lyophilisation cycle by loading the bag into a freeze dryer and operating the freeze dryer for a lyophilisation cycle. The lyophilisation cycle generally comprises at least a sublimation phase, optionally followed by a desorption phase.

Where lyophilisation is carried out in a freeze dryer, at least a portion of the bag may be open to provide access to the interior of the bag during lyophilisation. For example, the filling port may be open during the lyophilisation cycle. In such embodiments, the evaporative capacity of the bag having an open filling port:
  when measured at −10° C. and at 150 μbars may be about $0.8 \times 10^{-4}$, about $0.9 \times 10^{-4}$ or about $1.0 \times 10^{-4}$ kg/s/m$^2$,
  when measured at −10° C. and at 60 μbars may be about $0.7 \times 10^{-4}$, about $0.8 \times 10^{-4}$, or about $0.9 \times 10^{-4}$ kg/s/m$^2$,
  when measured at 0° C. and at 150 μbars may be about $1.5 \times 10^{-4}$, about $1.7 \times 10^{-4}$, or about $1.9 \times 10^{-4}$ kg/s/m$^2$, and/or
  when measured at 0° C. and at 60 μbars may be about $1.0 \times 10^{-4}$, about $1.2 \times 10^{-4}$, or about $1.4 \times 10^{-4}$ kg/s/m$^2$.

Additionally or alternatively, the global heat transfer coefficient (Kv) of the bag having an open filling port:
  when measured at −10° C. and at 60 μbars or 150 μbars may be about 0.007, about 0.008, or about 0.009,
  when measured at 0° C. and at 150 μbars may be about 0.01, about 0.012, about 0.013, about 0.014 or about 0.015, and/or
  when measured at 0° C. and at 60 μbars may be about 0.008, about 0.01, or about 0.012.

If the product to be lyophilised comprises live cells, the difference in viability as determined i) prior to the lyophilisation cycle and ii) following the lyophilisation cycle may be less than two orders of magnitude, or may be less than one order of magnitude.

Additionally or alternatively, prior to or during the lyophilisation cycle (for example prior to, during or following the sublimation phase) an opening may be made in the bag to provide access to its interior. For example, a portion of the flexible wall of the bag may be removed. In such embodiments, the evaporative capacity of the bag having a portion of its wall removed:

when measured at −10° C. and at 150 μbars may be about 1.2×10$^{-4}$, about 1.3×10$^{-4}$ or about 1.4×10$^{-4}$, or about 1.5×10$^{-4}$ kg/s/m$^2$, when measured at −10° C. and at 60 μbars may be about 1.0×10$^{-4}$, about 1.1×10$^{-4}$, or about 1.2×10$^{-4}$ kg/s/m$^2$, when measured at 0° C. and at 150 μbars may be about 1.7×10$^{-4}$, about 1.9×10$^{-4}$, or about 2.1×10$^{-4}$ kg/s/m$^2$, and/or when measured at 0° C. and at 60 μbars may be about 1.7×10$^{-4}$, about 1.9×10$^{-4}$, or about ×10$^{-4}$ kg/s/m$^2$.

Additionally or alternatively, the global heat transfer coefficient (Kv) of the bag having an open filling port:

when measured at −10° C. and at 150 μbars may be about 0.01, about 0.011, or about 0.012, when measured at −10° C. and at 60 μbars may be about 0.007, about 0.009, or about 0.01, when measured at 0° C. and at 150 μbars may be about 0.02, about 0.022, about 0.023, about 0.024 or about 0.025, and/or when measured at 0° C. and at 60 μbars may be about 0.012, about 0.014, or about 0.015.

To minimise the risk of contamination of the product within the bag, the area of the opening made in the wall of the bag may preferably be less than about 50%, less than about 40%, less than about 30%, less than about 20% or less than about 10% of the total area of the exterior of the bag.

By removing relatively small amounts of wall from the bag, the exposure of the interior of the bag to potential contamination is minimised and is far lower than for open trays used conventionally for lyophilisation.

In processes according to the invention in which an opening is made in the wall of the bag, the bag may be constructed to facilitate this. For example, the wall of the bag may be provided with a tear line, score line, or the like and/or a pull tab.

Additionally or alternatively, the bag may be provided with particulate barrier means. For example, this could take the form of a moisture permeable membrane (i.e. a membrane having a WVTR of at least about 500, at least about 1000, at least about 1500 or at least about 2000 g·m$^{-2}$·d$^{-3}$) or a component comprising such a membrane which closes an opening in the wall of the bag and/or the filling port to prevent the ingress of particulate contaminants into the interior of the bag, while permitting the egress of moisture therefrom.

Such a membrane may be provided as part of the bag (e.g. it may be applied to a region of the interior of the wall of the bag in which a portion of the wall of the bag will be removed to produce an opening, albeit one spanned by the membrane) and/or as a separate component, (e.g. a cap, for application to the filling port, partially formed of the membrane, configured such that when the cap is applied to the filling port, at least part of that port is spanned by the membrane).

While the use of such a membrane can prevent the ingress of particulate contaminants into the interior of the bag, as is demonstrated by the accompanying examples, it has advantageously been found that even without the use of such a barrier, comparable results, in terms of achieved moisture rates and absence of contaminants can be achieved using the process of the invention as compared to using the Lyoguard® tray.

The bag can be filled using any suitable technique or apparatus known to those skilled in the art. Prior to filling, one or more components of the product to be lyophilised may be blended. For example an active ingredient or an organism (e.g. a bacteria or fungus) may be blended with one or more excipients (e.g. lyoprotectants).

During the lyophilisation cycle, the filled bag may be manipulated. For example, the bag may be manually or mechanically shaken or moved in order to achieve uniform distribution of the product in the bag. Additionally or alternatively, as discussed above, an opening may be made in the wall of the bag to maximise egress of moisture therefrom. Such manipulations may be carried out at any time in the lyophilisation cycle and may be carried out once or repeatedly. For example, such manipulations may be carried out prior to, during and/or after the sublimation phase, and/or prior to, during or after the desorption phase.

Any suitable lyophilisation apparatus known to one skilled in the art may be employed in the process of the present invention. As mentioned above, in processes according to the present invention, the lyophilisation cycle may employ a sublimation phase. As part of this phase, the product may firstly be frozen. However, this is not compulsory as processes in which the product (or one or more components of the product) are frozen and maintained at frozen conditions prior to filling also fall within the scope of the present invention.

The process of the present invention may further comprise one or more steps which are carried out following completion of the lyophilisation cycle. For example, if the lyophilised product is not to be used in downstream processing steps immediately following completion of the lyophilisation cycle, the bag may be closed to conveniently permit storage of the lyophilised product in the bag without having to transfer the product into a separate container. Closure of the bag can be achieved by any suitable means known to those skilled in the art, for example: heat sealing the bag to close an opening formed in the wall and/or the filling port; applying closure means to close the filling port; and/or gluing or welding a part of the bag onto itself to close an opening formed in the wall of the bag and/or the filling port. In such cases, the bag may be provided with means to close an opening in the wall of the bag and/or filling port.

Other steps that may be carried out in processes of the invention after completion of the lyophilisation cycle include grinding the product and/or filling the product into capsules.

The present invention also provides a pharmaceutical product obtainable from the process described above.

The present invention also provides a bag for use in the process described above, the bag having an interior and an exterior defined by a flexible wall, the bag further comprising a filling port providing access to the interior of the bag.

BRIEF DESCRIPTION OF THE DRAWINGS

By way of example, one or more embodiments of the present invention will now be described with reference to the accompanying drawings in which:

FIG. 3 shows a plurality of bags which have been filled by a process according to the present invention, where the bags are stored in both a first vertical orientation and a second horizontal orientation;

FIG. 4A shows two perspective views and one end view of an unfilled bag for use in a process according to the present invention;

FIG. 4B shows a side and a front view of a bag that has been filled using a process according to the present invention;

DETAILED DESCRIPTION OF THE DRAWINGS

Example 1—Bulk Loading System

Figure 1:
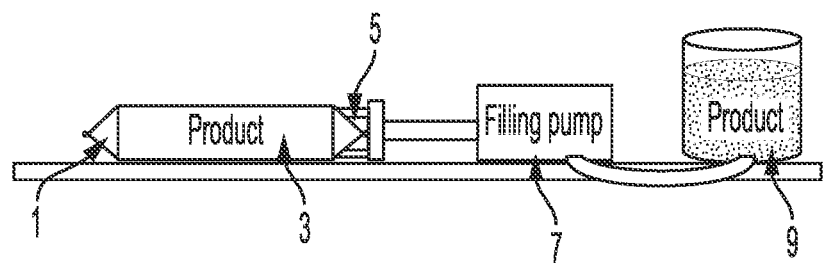
FIG. 1 is a schematic drawing of an apparatus for use in a process according to a first embodiment of the present invention, with a bag in a first filling orientation.

FIG. 1 illustrates a process for lyophilising a product according to the present invention in which a bulk product loading system in the form of a bag 1 is provided. The bag 1 has an interior and an exterior defined by a flexible wall. The bag 1 comprises a filling port 5 which provides access to the interior of the bag 1, and through which the interior of the bag 1 is filled with a product 3 having a first moisture content. The product 3 is pumped from a storage hopper 9 using a filling pump 7. In conventional systems, to minimise the risk of contamination, product is only filled into the lyophilisation try shortly prior to lyophilisation. This synchronisation of the filling and lyophilisation steps requires a high level of user attention and planning. In contrast, in the process of the present invention, given that the bag 1 may be fitted with a closure, once filling is completed, the bag 1 can be closed and stored until a time at which lyophilisation is to occur.

Figure 2:
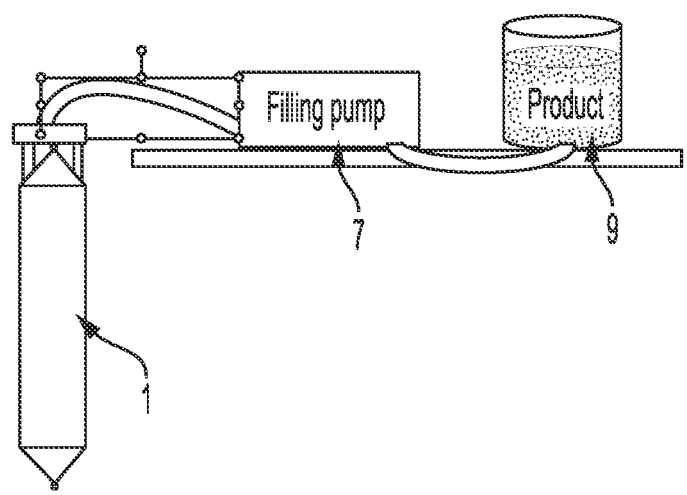
FIG. 2 is a schematic drawing of the apparatus of FIG. 1, with the bag in a second filling orientation.
Figure 5:
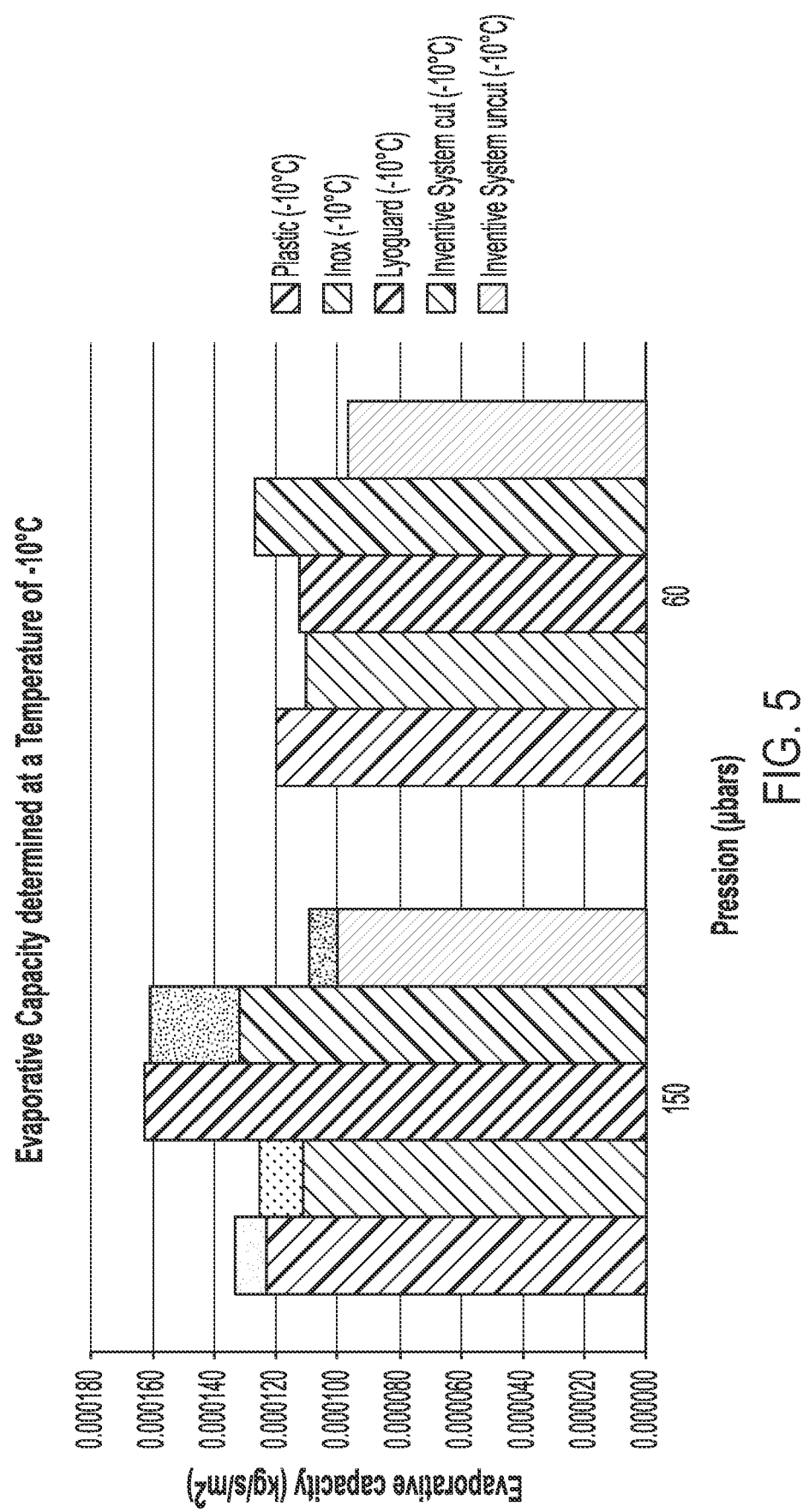
FIG. 5 is a graph showing a comparison of the evaporative capacity determined at a temperature of −10° C. for processes according to the present invention and processes using conventional lyophilisation apparatus.
Figure 6:
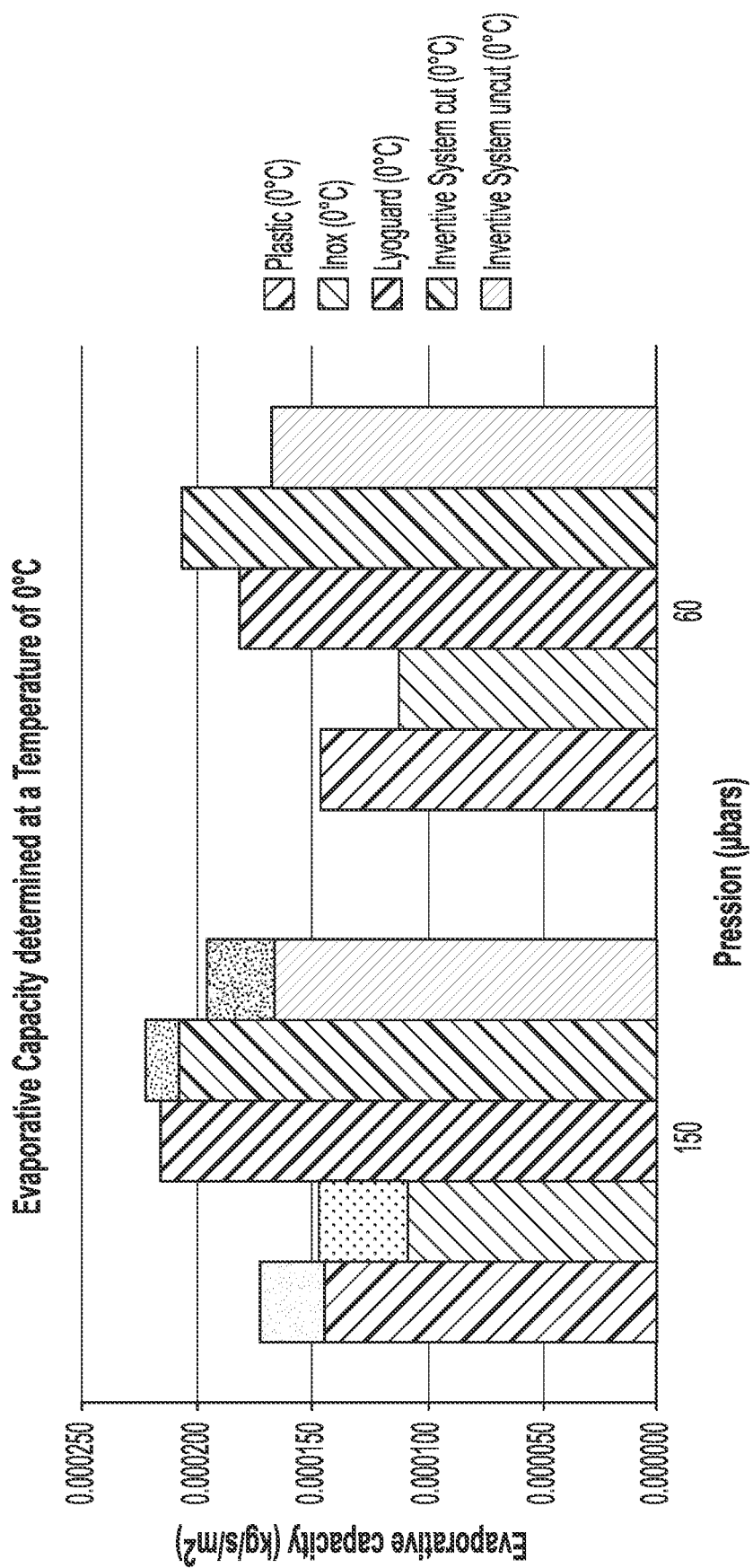
FIG. 6 is a graph showing a comparison of the evaporative capacity determined at a temperature of 0° C. for processes according to the present invention and processes using conventional lyophilisation apparatus.
Figure 7:
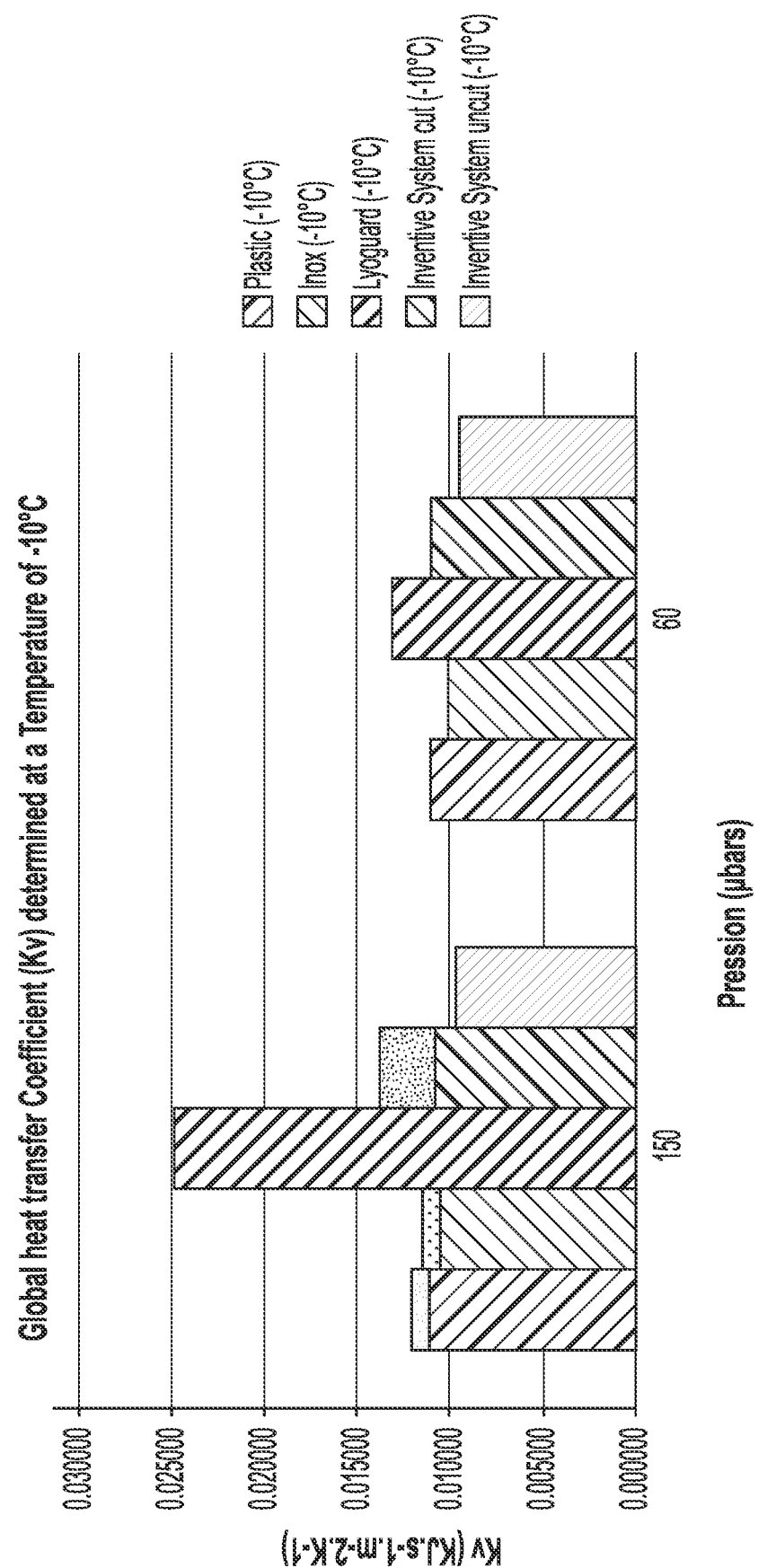
FIG. 7 is a graph showing a comparison of the Global heat transfer coefficient (Kv) determined at a temperature of −10° C. for processes according to the present invention and processes using conventional lyophilisation apparatus.
Figure 8:
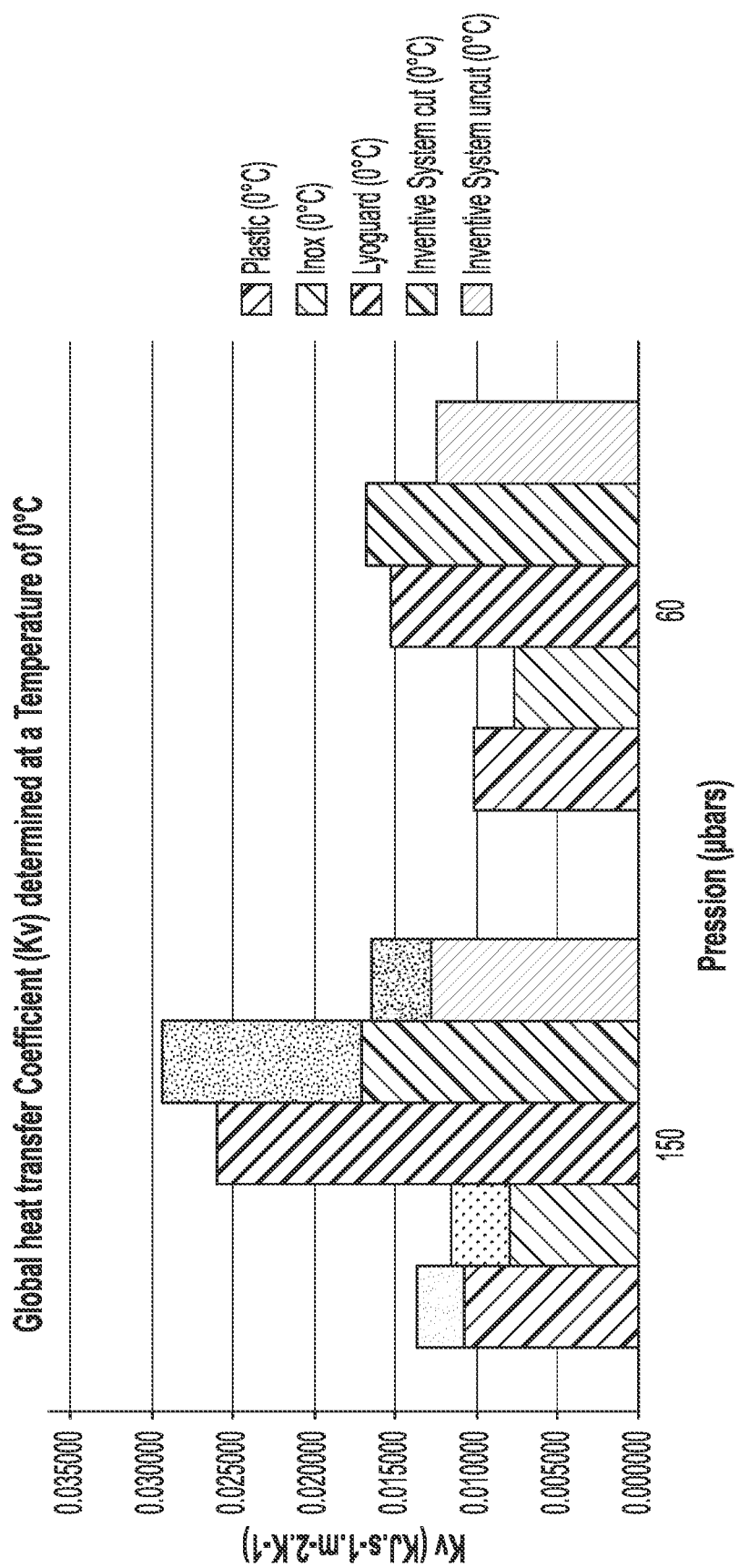
FIG. 8 is a graph showing a comparison of the Global heat transfer coefficient (Kv) determined at a temperature of 0° C. for processes according to the present invention and processes using conventional lyophilisation apparatus.

As can be seen in FIG. 1, owing to the dimensions of the bag 1, the product 3 stored therein has uniform thickness. This is advantageous as it facilitates the uniform removal of moisture from the product 3 during lyophilisation. Additionally, as shown in FIG. 2, the bag can be filled at different orientations and its dimensions cause the product to be distributed evenly; in FIG. 1 the bag 1 is filled in a horizontal orientation, and in FIG. 2 the bag is filled in a vertical orientation.

As can be seen from FIG. 3, the bags 1 can be loaded onto lyophilisation shelves at different orientations (for example, vertical or horizontal) without an unacceptable loss in uniformity of product.

FIGS. 4A and 4B provide a range views of the unfilled (FIG. 4A) and filled (FIG. 4B) bags 1. As can be seen from these figures, the bag 1 is provided with two planar panels 2 spaced apart by a side wall 4. The height of the side wall 4 is constant, meaning that the interior of the bag 1 has a relatively fixed height, ensuring that the product 3 filled therein is of uniform depth.

As is apparent from this example, the bags 1 used in the process of the present invention can be used continuously in several stages of the formulation process, from receiving and storing the moist product during storage, during lyophilisation, and during post-lyophilisation storage. Conventionally used lyophilisation trays could not be used for prolonged storage of pharmaceutical grade products, either pre- or post-lyophilisation.

Example 2—Performance of Processes According to the Present Invention Versus Processes Using Conventional Lyophilisation Apparatus Tests were conducted to evaluate the freeze drying performance of the process of the present invention as compared to processes using conventionally used apparatus. The bag of Example 1 was tested (both with its filling port opened (shown as "uncut") and with part of its exterior cut away (shown as "cut")) alongside a PETG plastic tray, a stainless steel tray (inox) and a Lyoguard tray. The containers were filled with water, frozen and freeze-dried for a defined period at two primary drying temperatures (−10° C. and 0° C.) and two chamber pressures (150 μbars and 60 μbars). The water quantity was measured, which enabled evaporative capacity and the global heat transfer coefficient, Kv, to be determined for each system. The results are shown in FIGS. 5 to 8.

As can be seen, the performance of the system of the invention was comparable to that of the Lyoguard tray. Advantageously, however, the bags employed in the present invention cost only a few euros to manufacture, whereas the Lyoguard trays retail at in excess of €100 per tray. Indeed, as can be seen from FIGS. 5 to 8, in some of the tests, the bag of the present invention out-performed the Lyoguard tray.

Example 3—Viability of Bacterial Strains Lyophilised Using the Process of the Present Invention Three compositions comprising separate bacterial strains (*Roseburia hominis* (Strain A), *Bifidobacterium breve* (Strain B) and *Enterococcus gallinarum* (Strain C)) as well as sucrose/cysteine lyoprotectants were filled into separate bags as described in Example 1 and then the bags were sealed by closing the filling ports. The contents of the bags were then frozen and the bags loaded into a freeze dryer. As this happened, the end of the bag furthest from the filling port was removed, exposing the interior of the bag, and the cut bag was then subjected to lyophilisation cycles, according to the conditions shown below:

| Strain A | Values |
| --- | --- |
| Temperature primary desiccation (PD) | −25° C. to −10° C. |
| Vacuum PD | 150 μbars |
| Temperature secondary desiccation (SD) | +25° C. |
| Vacuum SD | 50 μbars |

| Strain B | Values |
| --- | --- |
| Temperature primary desiccation (PD) | −30° C. to −10° C. |
| Vacuum PD | 50 μbars |
| Temperature secondary desiccation (SD) | +25° C. |
| Vacuum SD | 50 μbars |

| Strain C | Values |
| --- | --- |
| Temperature primary desiccation (PD) | −20° C. to +10° C. |
| Vacuum PD | 150 μbars |
| Temperature secondary desiccation (SD) | +25° C. |
| Vacuum SD | 50 μbars |

Bacterial cell counts were carried out before and after lyophilisation. The results are shown in the table below:

| Strain | Viability before freeze drying | Viability after freeze drying |
| --- | --- | --- |
| Strain A | $1.10^{10}$ CFU*/g dry matter | $1.10^{10}$ CFU/g dry matter |
| Strain B | $3.10^{11}$ CFU/g dry matter | $1.10^{11}$ CFU/g dry matter |
| Strain C | $4.10^{12}$ CFU/g dry matter | $2.10^{12}$ CFU/g dry matter |

*Colony Forming Units

As is apparent, the bags of Example 1 advantageously permitted three different bacterial strains to be lyophilised without any significant or unacceptable loss in viability.

It will be appreciated that the embodiments shown in the figures and described above are by way of example only, and that alterations or modifications may be made within the scope of the invention as defined in the following claims.

The invention claimed is:

1. A method of lyophilizing a product comprising:
   a. filling a product into an interior of a bag, wherein the product comprises pharmaceutical-grade live anaerobic bacterial cells having a first moisture content; and
   b. exposing the product to a lyophilization cycle in a lyophilizer via a portion of the bag which is open, wherein the first moisture content of the product is reduced to a second moisture content,
   wherein the bag has an evaporative capacity of:
   (i) at least about $0.8 \times 10^{-4}$ kg/s/m² when measured at −10° C. and at 150 μbars;
   (ii) at least about $0.7 \times 10^{-4}$ kg/s/m² when measured at −10° C. and at 60 μbars;
   (iii) at least about $1.5 \times 10^{-4}$ kg/s/m² when measured at 0° C. and at 150 μbars; or
   (iv) at least about $1.0 \times 10^{-4}$ kg/s/m² when measured at 0° C. and at 60 μbars.

2. The method of claim 1, wherein the bag has an evaporative capacity of about $0.9 \times 10^{-4}$ kg/s/m² when measured at −10° C. and at 150 μbars.

3. The method of claim 1, wherein the bag has an evaporative capacity of about $0.8 \times 10^{-4}$ kg/s/m² when measured at −10° C. and at 60 μbars.

4. The method of claim 1, wherein the bag has an evaporative capacity of about $1.7 \times 10^{-4}$ kg/s/m² when measured at 0° C. and at 150 μbars.

5. The method of claim 1, wherein the bag has an evaporative capacity of about $1.2 \times 10^{-4}$ kg/s/m² when measured at 0° C. and at 60 μbars.

6. The method of claim 1, wherein the interior of the bag is defined by a flexible wall of the bag.

7. The method of claim 1, wherein the bag has two generally coplanar walls spaced apart by a side wall when filled.

8. The method of claim 7, wherein the two coplanar walls are substantially coplanar flexible walls.

9. The method of claim 7, wherein the side wall has a substantially constant height.

10. The method of claim 7, wherein the product is exposed to the lyophilization cycle by removing a portion of a wall of the bag.

11. The method of claim 10, wherein the removing of the wall of the bag is carried out after commencement of the lyophilization cycle.

12. The method of claim 1, further comprising removing the product from the bag.

13. The method of claim 12, further comprising preparing a dosage form of the product.

14. The method of claim 13, wherein the preparing comprises filling a capsule with the product.

15. A method of lyophilizing a product comprising:
   a. filling a product into an interior of a bag, wherein the product comprises pharmaceutical-grade live anaerobic bacterial cells having a first moisture content; and
   b. exposing the product to a lyophilization cycle in a lyophilizer via a portion of the bag which is open, wherein the first moisture content of the product is reduced to a second moisture content,
   wherein the bag has a global heat transfer coefficient (Kv) of:
   (i) at least about 0.007 when measured at −10° C. and at 60 μbars or 150 μbars;
   (ii) at least about 0.01 when measured at 0° C. and at 150 μbars; or
   (iii) at least about 0.008 when measured at 0° C. and at 60 μbars.

16. The method of claim 15, wherein the bag has a global heat transfer coefficient (Kv) of about 0.008 when measured at −10° C. and at 60 μbars or 150 μbars.

17. The method of claim 15, wherein the bag has a global heat transfer coefficient (Kv) of about 0.012 when measured at 0° C. and at 150 μbars.

18. The method of claim 15, wherein the bag has a global heat transfer coefficient (Kv) of about 0.01 when measured at 0° C. and at 60 μbars.

19. The method of claim 15, wherein the bag has two generally coplanar walls spaced apart by a side wall when filled.

20. The method of claim 19, wherein the product is exposed to the lyophilization cycle by removing a portion of a wall of the bag.

* * * * *